Jan. 6, 1959 E. B. LE GRICE Plant Pat. 1,792
ROSA FLORIBUNDA PLANT
Filed Jan. 15, 1958
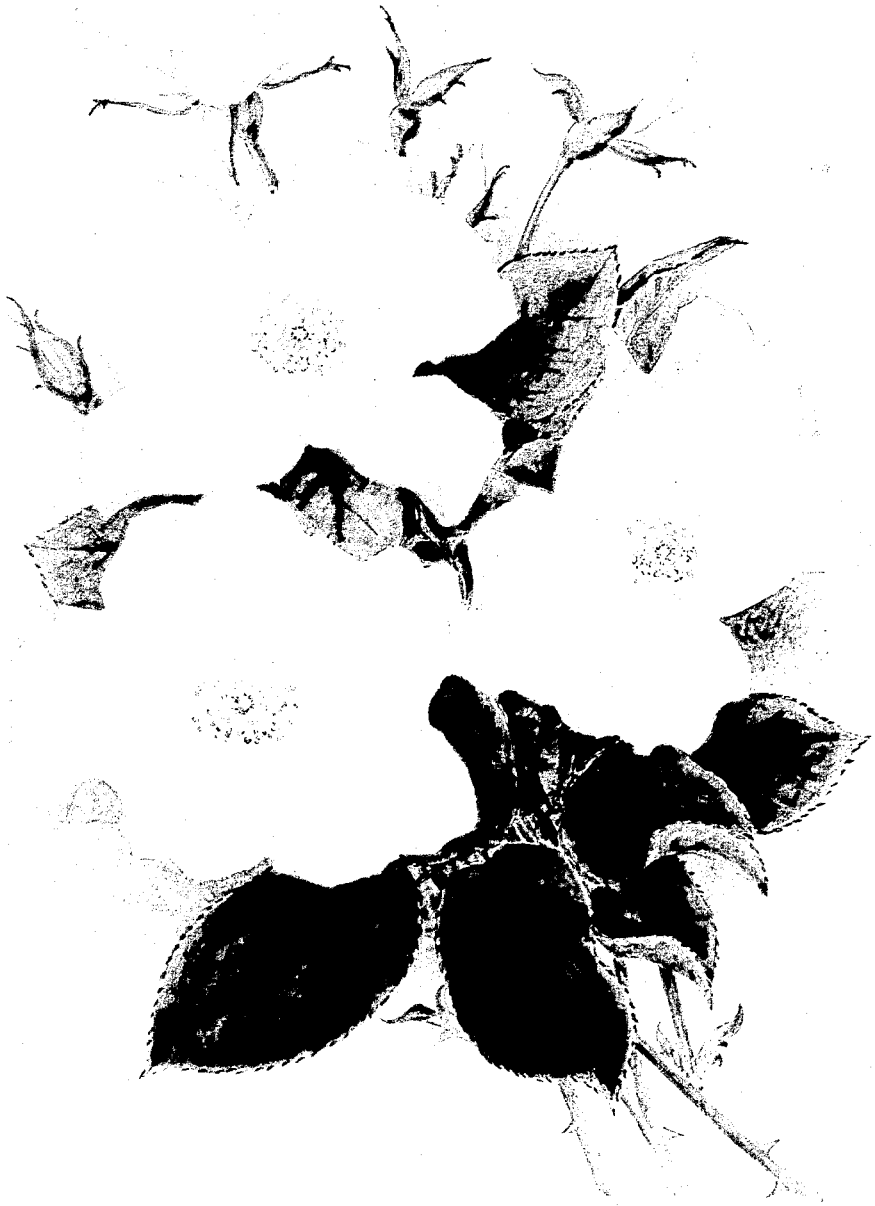
WITNESS
Addison E Avery
INVENTOR
Edward Burton Le Grice,
by: John H. Leonard,
his ATTY.

United States Patent Office

Plant Pat. 1,792
Patented Jan. 6, 1959

1,792

ROSA FLORIBUNDA PLANT

Edward Burton Le Grice, North Walsham, Norfolk, England

Application January 15, 1958, Serial No. 709,126

1 Claim. (Cl. 47—61)

This invention relates to a new variety of rose plant which is a Rosa Floribunda hybrid.

The present rose plant was produced originally by the deliberate crossing of a rose seedling No. 49.7, as a seed parent, with Mme. Pierre S. du Pont, of unknown parentage, an unpatented variety, as the pollen parent.

The seed parent, a rose seedling No. 49.7 was produced by a crossing of a rose Poulsen's Pink, an unpatented variety, and a rose Ellinor Le Grice, Plant Patent No. 917.

The new variety was asexually reproduced by me at North Walsham, England, by budding. The new variety has been tested in England.

The drawing shows in color a number of typical stalks with leaves, buds, blooms and thorns.

The exposed plant is in the form of a woody bush, symmetrical in shape and flattened on top. It grows generally to a height of about 2½ feet and has a spread of about 2 feet. It is a vigorous grower.

The exposed portion of the plant has good resistance to low temperature when protected and unprotected. Its resistance both to drought and to wet seasons is good.

For growth it prefers moderate sun and partial shade, with a west exposure. It thrives well in any medium loam soil of normal drainage.

The main stalks of the plant are branched and stiff. They are adequate to support the foliage and blooms well.

The new growth of the stalks range from Lettuce Green, Chart 861/3, through a Spinach Green, Chart 0960/3, streaked with Oxblood Red, Chart 00823. The old growth is somewhat darker.

The main stalks range from about 18 inches to 21 inches in length and are divergent. They have a prickly surface texture. The branches are whorled and of smooth texture with few thorns. They are numerous and stiff and, in general, are a Spinach Green, Chart 0960/3, sometimes tinged with Oxblood Red, Chart 00823.

The foliage, in general, is open, the leaf arrangement being whorled. The leaves are medium in quantity. The new leaves, on the top surface, are a Pod Green, Chart 061/1, shaded with Oxblood Red, Chart 00823/3, with the green predominant.

The old leaves, on the top surface, are Willow Green, Chart 000862, on the upper side shaded with Oxblood Red, Chart 00823/3. On the underside, the old leaves are Sage Green, Chart 000861. The serrated edges and veins on the upper surface are generally Oxblood Red, Chart 00823/3, on both the old and new leaves.

In general, the color of the old leaves is variegated, the variegation comprising the prominent reddish brown serrated edges of Oxblood Red, Chart 00823/3.

The leaves are of medium size, ranging from 4 to 6 inches in length and from 3 to 4 inches in width. They are of the usual shape, being pinnate with serrated margins, hastate bases, and acute apices. They have smooth glands and are of average thickness. They are glossy on the upper face and dull, smooth on the reverse. Their persistency on the plant is excellent. Each leaflet is positioned well apart from the others.

The petioles or leaf stems are a Lettuce Green, Chart 861, on the inner side, veined with Oxblood Red, Chart 00823/1. They average in length about 1¼ inches and are strong. They have a dull surface texture.

The stipules are Lettuce Green, Chart 861, and are veined and have fimbriated edges colored Oxblood Red, Chart 00823/1.

The plant grows and blooms well in temperate regions up to 750 feet above sea level. It prefers sun, western exposure, wet, cold seasons, and a rich, loamy, well drained, slightly acid soil of about pH 6.5. Changes in exposure, wetness, coldness of season and quality of soil do not cause much variation in the quality, quantity or color of blooms. They open well in all weathers and maintain their color.

The plant blooms from early June through October, this blooming being continuous for a period of about five months. Cutting of part of the flowers appears not to change the blooming characteristics or period.

As the conditions approach the preferred the blooms become of improved size. The color improves where the development can be slower. Otherwise these conditions make little difference.

The buds are of the usual size and shape and of smooth surface. They are borne upright as terminals. The petal color, when the sepals first divide, is Buttercup Yellow, Chart 5/3.

When the petals begin to unfurl the color is Buttercup Yellow, Chart 5/2, splashed with Scarlet, Chart 19/1. When half blown, the color is Indian Yellow, Chart 6/3, changing to Saffron Yellow, Chart 7/3, near the base and splashed slightly with Scarlet, Chart 19/1. When full blown, the principal color is Empire Yellow, Chart 603/3, with deeper Empire Yellow, Chart 603/1, at the base and slightly stained on the back with Carmine, Chart 21/1.

The sepals are of the usual shape and have slight spiculiform protuberances widely distributed on the surface. The sepals are of Lettuce Green, Chart 861, streaked with Oxblood Red, Chart 00823/1.

The calyx is of the same color as the sepals. It is usual in shape and size with a smooth surface texture.

The peduncles average from 1 to 5 inches in length and are Lettuce Green, Chart 861/3 on the exposed side with hairlike thorns of Oxblood Red, Chart 00823. They are of medium strength.

The pedicels average from 1 to 2 inches in length. Their color generally is Lettuce Green, Chart 861/3, on the exposed side with hairlike thorns of Oxblood Red, Chart 00823. They are strong.

An increase in the temperature tends to hasten the blooming of the plant.

The blooms are of the single type. They average from 3¼ to 3½ inches in diameter and an average plant will bear as many as 50 flowers at the same time. The blooms are borne singly and in racemes. On the plant, each flower lasts from two to three days and each flower head from 5 to 10 days. When cut, each flower lasts from 2 to 3 days and each flower head up to 7 days.

The petalage is Empire Yellow, Chart 603/3, the center or base being Empire Yellow, Chart 603/1. The reverse of the petals is white, slightly stained with Carmine, Chart 21/1, except at the base where they are of Empire Yellow, Chart 603/1.

The general tonality of the plant from a distance, when it is in bloom, is a white with a cream shading. The older blooms become creamy white and bleach with age.

The petals are thick and waxy. On the inside they are shiny and on the outside they are slightly veined. They are slightly waved on the outer edge. There are no petaloids. The petals are perfectly placed in slightly imbricated relation at their margins and form a circular flower. The persistence of the petals is good, the petals dropping cleanly when finished. The flower is a perfect single rose.

The fragrance of the blooms is an average brier quality perfume and lasts while the anthers last.

The stamens are normal and many and Straw Yellow, Chart 604/1. The filaments are of medium size, and, in color, Empire Yellow, Chart 603/3. The pollen is Empire Yellow, Chart 603/2. The styles and stigmas are Pod Green, Chart 061/3.

The styles are about ¼ of an inch in length. The stigmas are about 1/16 of an inch. Ovaries are medium. The fruit is usual.

On the main stalk, from the base of the plant, the thorns are few and, on the lateral stalks, they are vary few. They are long and stiff and colored Rhodinite Red, Chart 0022. They are unevenly distributed on the main stalk and on the laterals and none on the peduncles.

The drawing further illustrates the characteristics of the variety and the following tabulation is a detailed description of the new variety:

*General*

Parentage:
- *Seed parent.*—Rose seedling No. 49.7, resulting from a cross between Poulsen's Pink and Ellinor Le Grice.
- *Pollen parent.*—Mme. Pierre S. du Pont, parentage unknown.

Classification: Botanic—Rosa Floribunda hybrid.

*Flower*

Blooming habit:
- *Location where observations were made*:—Roseland Nurseries, North Walsham, England. National Rose Trial Grounds, St. Alban's, England.
- *Flowering*:—Continuous for about five months from early June until end of October.

Bud:
- *Size.*—Usual.
- *Form.*—Usual.
- *Color.*—When sepals first divide, petals are Buttercup Yellow, Chart 5/3. When petals begin to unfurl they are Buttercup Yellow, Chart 5/2, splashed with Scarlet, Chart 19/1 and when half blown, they are Indian Yellow, Chart 6/3, changing to Saffron Yellow, Chart 7/3 near the base and splashed slightly with Scarlet, Chart 19/1. When full blown, the principal color is Empire Yellow, Chart 603/3 with an Empire Yellow, Chart 603/1 at the base and slightly stained on the back with Carmine, Chart 21/1.
- *Sepals.*—Of usual shape and are Lettuce Green, Chart 861, streaked with Oxblood Red, Chart 00823/1.
- *Calyx.*—Of the same color as sepals. It is usual in shape with a smooth surface texture.
- *Peduncle.*—Length—from 1 to 5 inches. Aspect—tiny thorn-like hairs. Color—Lettuce Green, Chart 861/3 with hairs Oxblood Red, 00823.
- *Opening.*—Rapid, increases with temperature.

Bloom:
- *Size.*—3¼ to 3½ inches in diameter.
- *Borne.*—Singly and in racemes.
- *Stem.*—Length—1 to 2 inches; strong. Aspect—thick and waxy petals, shiny on inside and slightly veined on outside. Color—Lettuce Green, Chart 861/3 with hairlike thorns of Oxblood Red, Chart 00823.
- *Form.*—When first opened—petals open widely, overlapping slightly at edges, revealing anthers and, when fully opened, are circular.
- *Permanence.*—On the plant—about 2 to 3 days per flower and 4 to 10 days per flower head. When cut, 2 to 3 days per flower and 7 days per flower head.

Petalage:
- *Number of petals under normal conditions.*—5.
- *Color.*—Inside Empire Yellow, Chart 603/1 with Empire Yellow, Chart 601/1 near base.
- *Variegations.*—As per above. Reverse of petals white, slightly stained with Carmine, Chart 21/1.
- *Discoloration.*—Slight bleaching with age.

Petals:
- *Texture.*—Thick and waxy.
- *Appearance.*—Shiny inside, slightly veined on reverse side.
- *Form.*—Slightly rounded, lightly waved on outer edge with slight radial indentations from outer edge inwardly to midportion.
- *Arrangement.*—Perfectly placed, slightly over-lapping at margins and forming circular flower.
- *Petaloids in center.*—None .
- *Persistence.*—Uncut, good, when uncut—good, drop cleanly when finished.
- *Fragrance.*—Average brier.
- *Lasting quality.*—On plant, each flower 2 to 3 days, each flower head 5 to 10 days; when cut, each flower 2 to 3 days, flower heads up to 7 days.

Genital organs:
- *Stamens.*—Normal.
- *Color.*—Straw Yellow, Chart 604/1.
- *Arrangement.*—Regular.
- *Filaments.*—Medium.
- *Color.*—Empire Yellow, Chart 603/3.
- *Pollen.*—Empire Yellow, Chart 603/2.
- *Styles.*—¼ inch, color Pod Green, Chart 061/3.
- *Stigmas.*—About 1/16 inches, colored Pod Green, Chart 061/3.
- *Ovaries.*—Medium.

Fruit: Usual.

*Plant*

Form: A woody bush, symmetrical in shape and flattened on top.

Growth: Vigorous, height about 2½ feet, spread 2 feet.

Foliage: Open and whorled, medium in quantity.
- *Size.*—Medium length from 4 to 6 inches and width from 3 to 4 inches.
- *Quantity.*—Medium.
- *Color.*—New leaves, on top, Pod Green, Chart 061/1 shaded with Oxblood Red, Chart 00828/3 with green predominant. On bottom, Oxblood Red, Chart 00823/3 on Pod Green, Chart 061/1, with Red predominant. Old leaves, on top, Willow Green, Chart 000862 and, on bottom, Sage Green, Chart 000861.
- *Shape.*—Usual pinnate, serrated edges, hastate base and acute apices.
- *Texture.*—Upper face, glossy. Lower face, dull and smooth. Average thickness, borne whorled with each leaflet set well apart from the others.
- *Edge.*—Serrated, color Oxblood Red, Chart 00823/3.

Petiole: Length, about 1¼ inches, with dull surface texture. Color—Lettuce Green, Chart 861 on inside, inner side veined with Oxblood Red, Chart 00823/1.

Stipules: Lettuce Green, Chart 861, veined, with fimbriated edges, color Oxblood Red, Chart 00823/1.

Disease resistance: It has not been attacked by any disease.

Wood:
- *Newest wood.*—Color Lettuce Green, Chart 861/3 through Spinach Green, Chart 0960/3, streaked with Oxblood Red, Chart 00823.
- *Bark.*—Smooth with few thorns.
- *Old wood.*—Color, somewhat darker.
- *Bark.*—Prickly.

Thorns:
- *Quantity.*—On main stalks, few. On the laterals, very few.
- *Form.*—Long and stiff.

*Color.*—Rhodinite Red, Chart 0022.

*Position.*—Unevenly distributed on main stalks and laterals and none on peduncles.

Special characteristics of the new hybrid rose plant are the perfection of the separate flowers, the abundance of its growth, and the large flower heads. The main distinguishing characteristics are that the blooms are exquisite, being unique in color, shape and freedom. The ability of the blooms to open from a tight bud when cut and to develop in water and last for a considerable time. The abundant foliage, and the strong, but bushy, growth which make it suitable for bedding.

Having shown and described my new variety of Rosa Floribunda plant and its manner of asexual reproduction, I claim:

The new and distinct variety of Rosa Floribunda plant herein shown and described.

No references cited.